(12) United States Patent
Chung

(10) Patent No.: US 9,636,493 B2
(45) Date of Patent: May 2, 2017

(54) MULTI-LUMEN TUBING TO SINGLE LUMEN TUBING CONNECTOR

(71) Applicant: Fenwal, Inc., Lake Zurich, IL (US)

(72) Inventor: Terry Chung, Kileer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 96 days.

(21) Appl. No.: 13/786,175

(22) Filed: Mar. 5, 2013

(65) Prior Publication Data

US 2013/0304039 A1    Nov. 14, 2013

Related U.S. Application Data

(60) Provisional application No. 61/644,282, filed on May 8, 2012.

(51) Int. Cl.
*A61M 39/10* (2006.01)
*A61M 39/08* (2006.01)

(52) U.S. Cl.
CPC ..... *A61M 39/105* (2013.01); *A61M 2039/082* (2013.01); *Y10T 29/49778* (2015.01)

(58) Field of Classification Search
CPC .... A61M 39/10; A61M 39/105; A61M 39/14;
A61M 2039/1077; A61M 2039/082;
A61M 39/20; F16L 37/56; F16L 31/00;
F16L 39/02; F16L 39/00; B04B 5/0442;
B04B 2005/045
USPC ........... 604/533, 534, 535; 285/122.1, 124.1, 285/124.3, 125.1, 129.1
See application file for complete search history.

(56) References Cited

U.S. PATENT DOCUMENTS

| 4,508,367 | A | | 4/1985 | Oreopoulos et al. |
| 4,670,009 | A | * | 6/1987 | Bullock .................. 604/533 |
| 5,551,942 | A | * | 9/1996 | Brown et al. ............... 494/45 |
| 5,996,634 | A | * | 12/1999 | Dennehey ............. B04B 5/0442 138/109 |
| 8,257,239 | B2 | | 9/2012 | Manzella et al. |
| 8,323,265 | B2 | | 12/2012 | Heaton |
| 2005/0256461 | A1 | * | 11/2005 | DiFiore ............ A61M 25/0075 604/247 |
| 2005/0267445 | A1 | * | 12/2005 | Mendels ...................... 604/534 |

* cited by examiner

*Primary Examiner* — Nathan R Price
*Assistant Examiner* — Weng Lee
(74) *Attorney, Agent, or Firm* — Foley & Lardner LLP

(57) ABSTRACT

A connector for a fluid handling system includes a body defining a plurality of internal passages that connect single-lumen tubes to lumens of a multi-lumen tube. Openings located along an internal edge of connector provide fluid communication between the internal passages and openings located along a curved outer surface of the multi-lumen tube.

7 Claims, 2 Drawing Sheets

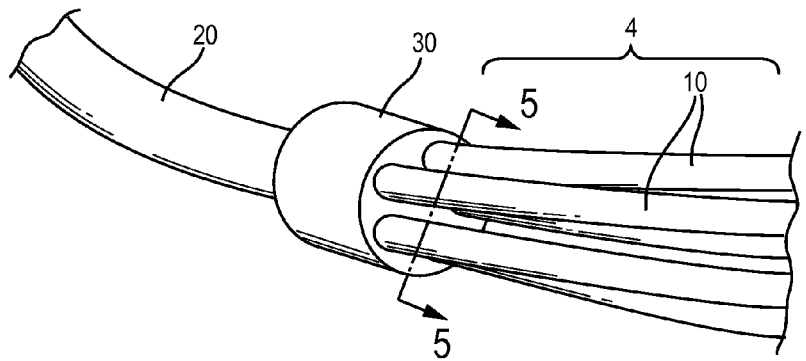
FIG. 2
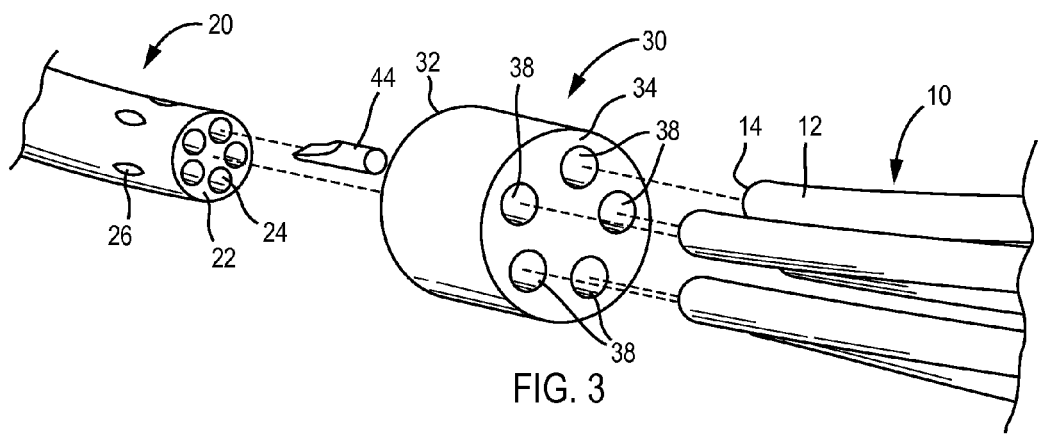
FIG. 3
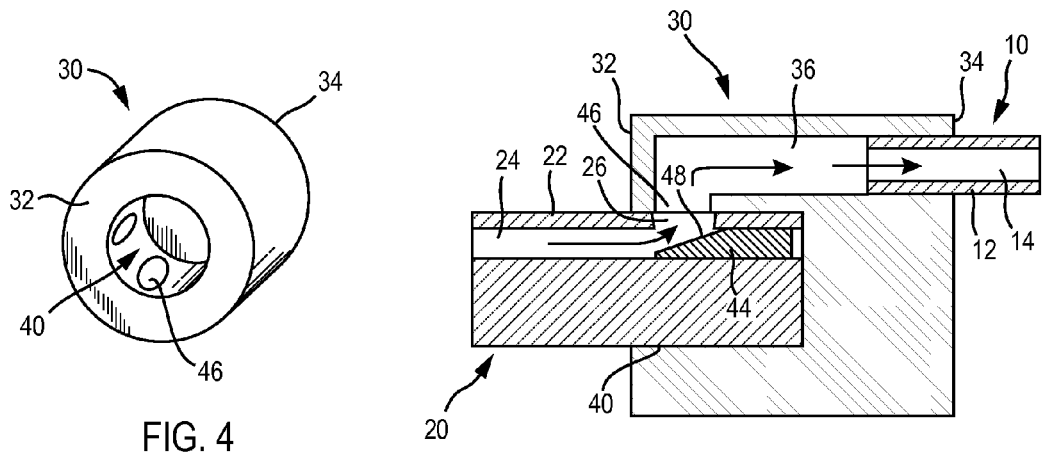
FIG. 4
FIG. 5

MULTI-LUMEN TUBING TO SINGLE LUMEN TUBING CONNECTOR

CONTINUITY DATA

The present application claims priority to U.S. Provisional Application No. 61/644,282, entitled "MULTI-LUMEN TUBING TO SINGLE LUMEN TUBING CONNECTOR," and filed May 8, 2012, the entirety of which is hereby incorporated by reference.

BACKGROUND

In medical settings, a biological fluid or medicament may be withdrawn from a subject or provided to a subject via a fluid handling system. For example, apheresis machines are generally configured to separate blood extracted from a subject into its constituent components (e.g., red blood cells, platelets, plasma, etc.). The blood or blood components may then be routed via a fluid handling system into different collection bags. In some cases, fluids flowing through such a fluid handling system may be divided into separate streams using a multi-lumen tube (e.g., a tube having multiple fluid paths), each lumen configured to carry a direct fluid or mixture. For example, a multi-lumen tube may be used in an apheresis system to transport whole blood or separated blood components (e.g., platelets, plasma, etc.) between the various portions of the system (e.g., a pump, a cassette, a flexible bag, a centrifuge or other blood separation mechanism, etc.).

A coupler may be used to convert a multi-lumen tube into multiple single-lumen tubes or vice-versa. For example, an adapter bushing may be inserted into the end of the multi-lumen tube to couple one of the lumens of the tube to a single-lumen tube. However, such an inserted member also substantially reduces the cross-section area of the lumen. In an apheresis or other blood-handling system, this may lead to increased hemolysis, which is a breaking or fracturing of red blood cells. Overmolded connectors may also be utilized, but can be relatively expensive components. Further, a multi-lumen tubing held in place with pins during the overmolding process can result in damage being caused to the relatively thin lumen walls of the multi-lumen tube.

SUMMARY

One embodiment relates to a connector for a fluid handling system. The connector includes a body defining a plurality of internal passages. The body has a first end face defining a plurality of openings each configured to receive a single-lumen tube. The body also has a second end face that defines a main opening configured to receive a multi-lumen tube and a plurality of openings located along an internal edge of the main opening. The plurality of openings located along the internal edge of the main opening are configured to engage openings located along a curved outer surface of the multi-lumen tube. Each of the plurality of internal passages defined by the body are configured to provide fluid communication between one of the plurality of openings of the first end face and one of the openings located along the internal edge of the main opening of the second end face.

Another embodiment relates to a method of attaching a multi-lumen tube to a single-lumen tube assembly. The method includes providing a connector body defining a plurality of internal passages. The body has a first end face defining a plurality of openings each configured to receive a single-lumen tube and has a second end face that defines a main opening configured to receive a multi-lumen tube and a plurality of openings located along an internal edge of the main opening. The plurality of openings located along the internal edge of the main opening are configured to engage openings located along a curved outer surface of the multi-lumen tube. Each of the plurality of internal passages defined by the body are configured to provide fluid communication between one of the plurality of openings of the first end face and one of the openings located along the internal edge of the main opening of the second end face. The method also includes inserting a plurality of single-lumen tubes into the openings of the first end face of the connector body. The method further includes aligning the openings located along the curved outer surface of the multi-lumen tube with the openings located along the internal edge of the main opening of the connector body. The method yet further includes inserting the multi-lumen tube into the main opening of the connector body.

A further embodiment relates to a connector for a fluid handling system. The connector includes first receiving means for receiving a multi-lumen tube having openings located along a curved outer surface of the multi-lumen tube. The connector also includes second receiving means for receiving a plurality of single-lumen tubes. The connector further includes connector means for communicating a flow of fluid between one of the openings located along the curved outer surface of the multi-lumen tube and one of the plurality of single-lumen tubes.

BRIEF DESCRIPTION OF THE DRAWINGS

Features, aspects, and advantages of the present invention will become apparent from the following description, appended claims, and the accompanying exemplary embodiments shown in the drawings, which are briefly described below.

FIG. 2 is an enhanced view of a connector for the fluid handling system of FIG. 1, according to an exemplary embodiment.

FIG. 3 is an exploded view of the connector of FIG. 2, according to an exemplary embodiment.

FIG. 4 is a rear isometric view of the connector of FIG. 2, according to an exemplary embodiment.

FIG. 5 is a cross-section view of the connector of FIG. 2, shown coupled to a multi-lumen tube and a single-lumen tube, according to an exemplary embodiment.

Like reference numbers and designations in the various drawings indicate like elements.

DETAILED DESCRIPTION OF THE EXEMPLARY EMBODIMENTS

Figure 1:
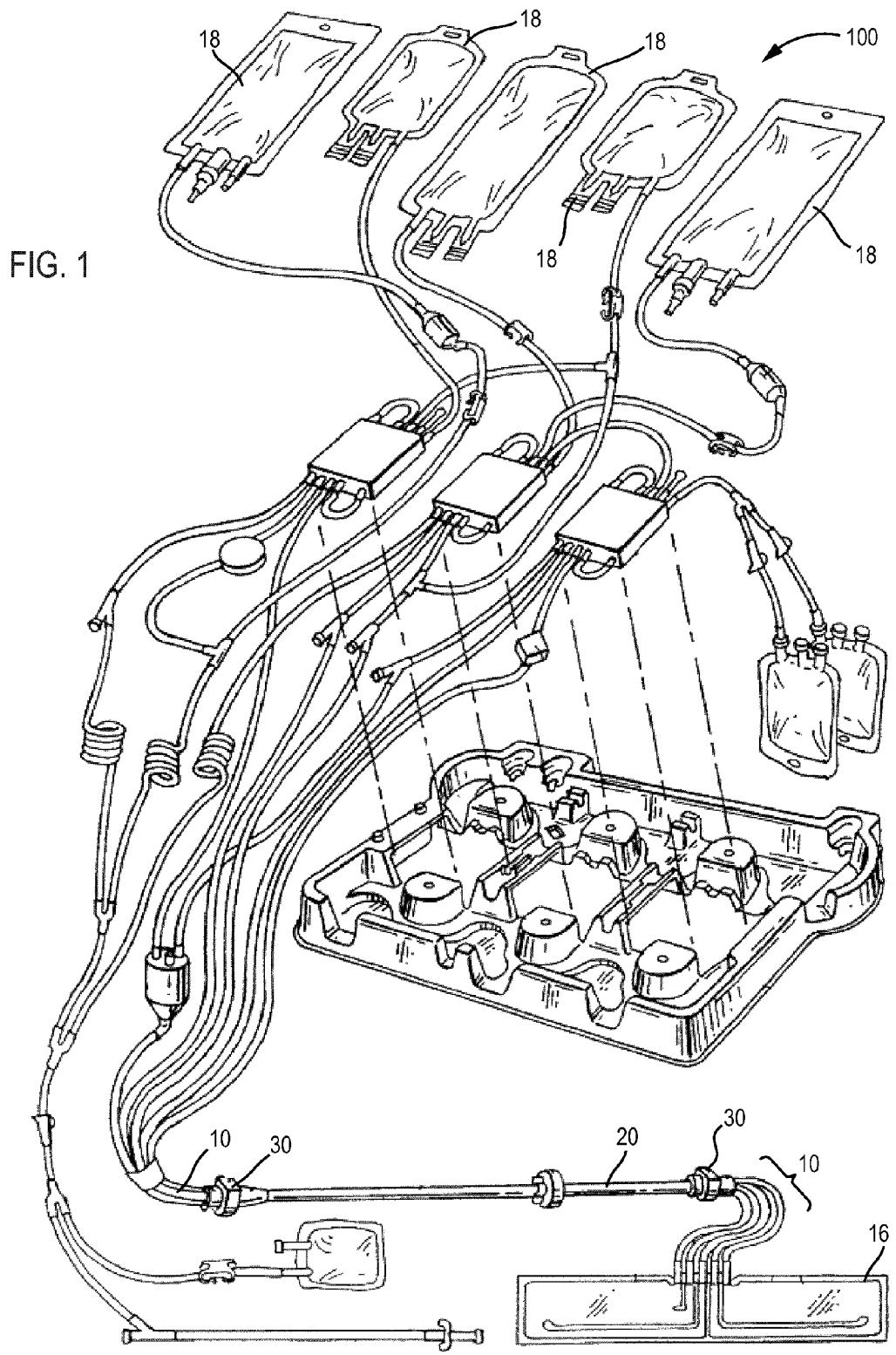
FIG. 1 is a schematic view of a fluid handling system, according to an exemplary embodiment.

It is to be understood that the following detailed description is exemplary and explanatory only, and is not restrictive of the invention as claimed. One or more embodiments may allow for an improved bonding between components of a fluid handling system. While primarily described herein with reference to a fluid handling system used in an apheresis machine, the described concepts may be applied to any other type of fluid handling system that use tubing and connectors. Other exemplary fluid handling systems may include, but are not limited to, fluid handling systems used in dialysis machines, systems configured to remove a biological fluid from a subject (e.g., blood, urine, etc.), systems configured to supply a biological fluid to a subject, systems configured to provide a medicament to a subject, and other such systems.

Referring now to FIG. 1, a fluid handling system 100 is shown, according to an exemplary embodiment. In various embodiments, fluid handling system 100 is part of an apheresis machine that separates blood drawn from a subject into blood components. For example, the apheresis machine may include a processing chamber 16 in which blood is separated into its constituent components (e.g., red blood cells, plasma, platelets, etc.) by a centrifuge or other blood separation mechanism. Fluid handling system 100 may then divert blood or blood components from processing chamber 16 to collection bags 18. For example, one of collection bags 18 may receive plasma separated from whole blood by processing chamber 16. In various embodiments, the tubing and other components of fluid handling system 100 is formed using non-reactive materials that are suitable for handling biological fluids (e.g., blood, etc.) and may be configured for a single use (e.g., intended to be disposed after each use). The tubing of fluid handling system 100 may also be formed using a relatively flexible material, such as PVC or silicone.

According to various embodiments, fluid handling system 100 utilizes both single-lumen tubes 10 and multi-lumen tubes 20. For example, blood or separated blood components may be diverted from processing chamber 16 via a plurality of single-lumen tubes 10 towards collection bags 18 (e.g., each of tubes 10 defines a hollow conduit through which a single stream of fluid may be conveyed). Fluid handling system 100 may also include one or more multi-lumen tubes 20 which each define multiple hollow conduits through which different streams of fluids may be conveyed. Multi-lumen tubes 20 may include any number of different fluid conduits. For example, multi-lumen tubes 20 may include five conduits, thereby allowing the simultaneous conveyance of five different streams of blood or blood components through the same piece of tubing.

Fluid handling system 100 may also include one or more connectors 30 configured to connect a multi-lumen tube 20 to one or more of single-lumen tubes 10. For example, the single-lumen tubes 10 that receive blood or blood components from processing chamber 16 may feed their respective streams of fluids into a single length of multi-lumen tube 20 via a connector 30. The length of multi-lumen tubing 20 may then convey the plurality of fluid streams towards their respective collection bags 18. In some embodiments, a connector 30 may be configured to allow fluid to flow from single-lumen tubes 10 into a multi-lumen tube 20. In other embodiments, a connector 30 may be configured to allow fluid to flow from a multi-lumen tube 20 to one or more single-lumen tubes 10.

Referring now to FIG. 2, an enhanced view of a connector 30 for fluid handling system 100 is shown, in accordance with an exemplary embodiment. As shown, connector 30 may be a rigid or semi-rigid connected to a set 4 of single-lumen tubes 10. Set 4 may include any number of single-lumen tubes 10, in various embodiments. For example, set 4 may include five single-lumen tubes 10 that are connected to connector 30. Also as shown, the opposite end of connector 30 may be connected to a multi-lumen tube 20. According to various embodiments, connector 30 and the tubes 10 and 20 are permanently bonded together to form hermetic seals and prevent the escape of fluid from fluid handling system 100 at the junctions between connector 30 and the tubes 10 and 20. In some embodiments, single-lumen tubes 10 and multi-lumen tube 20 may each be coupled to connector 30 with a solvent or adhesive. For example, a solvent or adhesive may be applied to the ends of tubes 10 and 20 prior to insertion into connector 30.

Referring now to FIG. 3, an exploded view of connector 30 is shown, according to an exemplary embodiment. Connector 30 may be a rigid or semi-rigid body with a first end face 32 configured to receive a multi-lumen tube 20 and a second end face 34 opposite first end face 32 configured to receive multiple single-lumen tubes 10. The body of connector 30 may be cylindrical in shape or may be of any other shape (e.g., ovoid, square, rectangular, etc.). Each of single-lumen tubes 10 may be a simple tube with a cylindrical wall 12 defining a single lumen 14 (e.g., a hollow fluid passage through the tube). Multi-lumen tube 20 includes a body defining multiple, parallel lumens 24. In comparison to single-lumen tubes 10, multi-lumen tube 20 may minimize the clutter and complexity of fluid handling system 100. Each of the lumens 24 in multi-lumen tube 20 may be utilized to transport fluids in either direction to or from different components of fluid handling system 100. For example, if multi-lumen tube 20 has five lumens 24, one of lumens 24 may transport whole blood in one direction (e.g., from a pump, collection bag, or cassette to a processing chamber), and the other four lumens 24 may transport blood and blood components (e.g., whole blood, red blood cells, platelets, and plasma) in the opposite direction (e.g., from the processing chamber to a pump, bag, or cassette).

Referring now to FIGS. 3-4, connector 30 may be configured to connect single-lumen tubes 10 and multi-lumen tube 20 such that losses to the fluid flow rates through connector 30 are minimized. In a blood handling system, for example, obstructions to the flowing fluids may cause hemolysis, a condition in which red blood cells are damaged and can result from collisions with the obstructions in the tubing. FIG. 4 is a rear isometric view of connector 30, showing end face 32 of connector 30 in more detail. In some embodiments, connector 30 includes internal passages 36 such that each of the lumens 24 in the multi-lumen tube 20 is in fluid communication with one of the single-lumen tubes 10. Single-lumen tubes 10 are each inserted into openings 38 on the second end face 34, as shown in FIG. 3. The outside surface of single-lumen tube 10 may be bonded to the inner surface of the corresponding opening 38. For example, a solvent or adhesive may be applied to the exterior surface of a single-lumen tube 10, the inner surface of an opening 38, or both, to form a hermetic seal between the single-lumen tube 10 and connector 30.

In some embodiments, end face 32 of connector 30 may form a central opening 40 into which multi-lumen tube 20 is inserted. The outside surface of multi-lumen tube 20 may also be bonded to the inner surface of the central opening 40. For example, a solvent or adhesive may be applied to the inner surface of opening 40 on connector 30, the outer surface of multi-lumen tube 20, or both, prior to insertion. By bonding the outer surface of multi-lumen tube 20 to the inner surface of central opening 40, the bonding surface area is also maximized, thereby improving the connection between tubes 10 and 20 and connector 30.

The mating end of multi-lumen tube 20 includes openings 26 on its exterior surface 22 that extend through to lumens 24, according to various embodiments. In some embodiments, openings 26 are skived openings. In other embodiments, openings 26 may be otherwise formed, such as by a punching process, a laser cutting process, etc. Openings 26 may also be of any shape (e.g., circular, ovoid, etc.). Central opening 40 of connector 30 may also include openings 46, which form channels through connector 30 to openings 38 on end face 34. Openings 26 of multi-lumen tube 20 are aligned with the corresponding radial openings 46 of connector 30 when the multi-lumen tube 20 is fully inserted into the central opening 40 of connector 30. Proper rotational alignment of multi-lumen tube 20 and connector 30 (and, therefore, rotational alignment of openings 26 and openings 46) may be achieved through a variety of features or indicia. For example, multi-lumen tube 20 and connector 30 may each have a surface indicator, such as a simple line or an arrow. The indicator may be printed or drawn or inscribed on the exterior surface of multi-lumen tube 20. In other embodiments, multi-lumen tube 20 and connector 30 may each have a matching flat on the mating surface (e.g., the end of multi-lumen tube 20 and opening 40 each form a circular shape having an arc and a flat portion connecting ends of the arc). In another embodiment, multi-lumen tube 20 may include a ridge or protrusion that is received in a groove formed in opening 40 of connector 30 or vice-versa. As opposed to using inserts to connect tubes 10 and 20 to connector 30 that reduce the diameter of lumens 14 and 24 thereby restricting fluid flow rates and/or causing hemolysis in a blood handling system, bonding the outside surfaces of tubes 10 and 20 to connector 30 does not obstruct lumens 14 and 24 or the fluid flow rates through tubes 10 and 20.

In some embodiments, the ends of the lumens 24 on surface 22 of multi-lumen tube 20 may be closed with plugs 44. Plugs 44 may be configured to force fluids flowing through multi-lumen tube 20 through openings 26 instead of through surface 22. In various embodiments, plugs 44 may be curved, tapered, or otherwise shaped such that they reroute the flow of fluids through openings 26 while minimizing the obstructions to the flows. In one embodiment, plugs 44 are separate, solid plugs that may be affixed in the lumens 24 (e.g., with a solvent or adhesive, with a heat seal, etc.) or may be coupled to multi-lumen tube 20 with an interference fit. In other embodiments, plugs 44 may be formed in lumens 24 with a compound, such as an epoxy resin. In further embodiments, plugs 44 may be formed within main opening 40 of connector 30 (e.g., plugs 44 may be integral to connector 30 within main opening 40). Plugs 44, like connector 30, multi-lumen tube 20, and single-lumen tubes 10 may be formed of a biologically inert material, in various embodiments.

Referring now to FIG. 5, a cross-section view of connector 30 is shown coupled to multi-lumen tube 20 and one of single-lumen tubes 10, according to an exemplary embodiment. In the example shown, multi-lumen tube 20 has been inserted into main opening 40 of connector 30 such that openings 26 of tube 20 are aligned with openings 46 of connector 30. On the opposite end of connector 30, one of single-lumen tubes 10 has been inserted into one of openings 38 of connector 30. Passage 36 internally connects opening 38 to opening 46 within connector 30, thereby allowing fluid to flow within connector 30 between openings 38 and 46. According to various embodiments, openings 46 are formed substantially perpendicular to passages 36 of connector 30. With multi-lumen tube 20 and the single-lumen tubes 10 coupled to connector 30 and skived openings 26 aligned with openings 44, each of lumens 24 in multi-lumen tube 20 is in fluid communication with one of the single-lumen tubes 10 through one of the internal passages 36 of connector 30. Plugs 44 prevent fluid from collecting downstream of the skived openings 26 (e.g., the portion of lumens 24 between openings 26 and the end or front face of the multi-lumen tube 20).

As shown, one of plugs 44 may have an inclined (e.g., angled, sloped, slanted etc.) surface 48 that turns the potentially high velocity flow through lumen 24 of multi-lumen tube 20 and directs the flow into passage 36 of connector 30. In some cases, inclined surface 48 may reduce hemolysis, since it minimizes the obstruction to the fluid flow through connector 30. The fluid redirected from multi-lumen tube 20 to passage 36 then flows through connector 30 and into single lumen tube 20. In other embodiments, the flow of fluid through connector 30 may be reversed (e.g., the fluid may alternatively flow from single-lumen tube 10 to multi-lumen tube 20 through connector 30). In some embodiments, each of the internal passages 36 within connector 30 may be configured to redirect fluid flow to a different direction (e.g., substantially ninety degrees relative to the direction of flow through lumens 24, at an angle ranging from zero to ninety degrees relative to the direction of flow through lumens 24, etc.) between opening 46 of passage 36 and opening 38 interfacing with the corresponding single-lumen tube 10. In one embodiment, internal passages 36 may have an internal width greater than an internal width of the lumens 24 of the multi-lumen tube. In some embodiments, fluid does not flow out of flat surface 22 of the multi-lumen tube 20, but instead is redirected by plugs or other obstructions to exit out openings in the curved, elongated surface of tube 20. In some embodiments, connector 30 is configured to not receive fluid flow via tubing inserted within openings on the flat surface 22 of multi-lumen tube 20.

The construction and arrangement of the elements of the connector as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations.

Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims.

While the exemplary embodiments are shown with respect to a blood flow distribution device, the connector may in alternative embodiments be implemented in a system for diverting other fluids, such as consumable fluids (e.g., beverages, syrups, etc.) or may be used in a manufacturing setting to approximately evenly distribute a single flow of a fluid to a plurality of destinations for the fluid. Any number of finished goods containers can be coupled to the connector to receive the fluids.

What is claimed is:

1. A fluid handling system comprising:
a plug;
a multi-lumen tube including:
    a curved outer surface; and
    a plurality of lumens, each lumen including a corresponding end opening extending through to the corresponding lumen and a corresponding surface opening located on the curved outer surface and extending through to the corresponding lumen, each surface opening located along the curved outer surface, each lumen configured such that inserting the plug into the corresponding end opening redirects a flow of fluid through the corresponding surface opening;
at least one single-lumen tube; and
a connector comprising:
    a body defining a plurality of internal passages, the body comprising:
    a first end face defining a plurality of openings each configured to receive the at least one single-lumen tube, and
    a second end face that defines a main opening configured to receive the multi-lumen tube,
    wherein a plurality of openings are located along an internal surface of the main opening, the plurality of openings located along the internal surface of the main opening being configured to engage the surface openings located along the curved outer surface of the multi-lumen tube;
    wherein each of the plurality of internal passages defined by the body are configured to provide fluid communication between one of the plurality of openings of the first end face and one of the openings located along the internal surface of the main opening of the second end face; and
    wherein the plug is configured for insertion into the corresponding end opening of a lumen of the multi-lumen tube, wherein the plug is configured to close the corresponding end opening and redirect a flow of fluid through the corresponding surface opening and one of the plurality of openings located along the internal surface of the main opening of the connector.

2. The fluid handling system of claim 1, wherein the plug comprises an inclined surface configured to redirect the flow of fluid.

3. The fluid handling system of claim 1, wherein the plug is integral to the body of the connector.

4. The fluid handling system of claim 1, wherein the plurality of openings located along the internal surface of the main opening are substantially perpendicular to the plurality of internal passages of the connector.

5. A fluid handling system comprising:
plug means;
a multi-lumen tube including:
    a curved outer surface; and
    a plurality of lumens, each lumen including a corresponding end opening extending through to the corresponding lumen and a corresponding surface opening located on the curved outer surface and extending through to the corresponding lumen, each surface opening located along the curved outer surface, each lumen configured such that inserting the plug means into the corresponding end opening redirects a flow of fluid through the corresponding surface opening;
a plurality of single-lumen tubes; and
    a connector comprising:
    first receiving means for receiving the multi-lumen tube;
    second receiving means for receiving the plurality of single-lumen tubes;
    connector means for communicating a flow of fluid between one of the surface openings and one of the plurality of single-lumen tubes; and
    the plug means for insertion into the corresponding end opening of a lumen in the multi-lumen tube and for redirecting a flow of fluid through the corresponding surface opening of the lumen.

6. The fluid handling system of claim 5, further comprising:
means for adhering the curved outer surface of the multi-lumen tube and the first receiving means.

7. The fluid handling system of claim 6, further comprising:
means for adhering the single-lumen tubes to the second receiving means.

* * * * *